United States Patent
Sunouchi et al.

[11] Patent Number: 5,368,043
[45] Date of Patent: Nov. 29, 1994

[54] MEASURING SYSTEM FOR VITAL MUSCLE ACTIVITY

[76] Inventors: Yujiro Sunouchi, 217, Fukuma-machi, Munakata-gun, Fukuoka-ken; Hiroshi Sakamoto, 388-3, Tsuboi 6-chome, Kumamoto-shi, Kumamoto-ken, both of Japan

[21] Appl. No.: 71,172
[22] Filed: Jun. 2, 1993

Related U.S. Application Data

[63] Continuation-in-part of Ser. No. 55,921, Apr. 29, 1993, which is a continuation of Ser. No. 795,428, Nov. 20, 1991, abandoned.

[30] Foreign Application Priority Data

| Jun. 3, 1992 | [JP] | Japan | 4-166721 |
| Aug. 7, 1992 | [JP] | Japan | 4-231481 |
| Apr. 2, 1993 | [JP] | Japan | 4-098364 |

[51] Int. Cl.⁵ ............................................. A61B 5/0488
[52] U.S. Cl. ........................................ 128/733; 128/777
[58] Field of Search ............... 128/733, 779-780, 128/731-732, 777, 774

[56] References Cited

U.S. PATENT DOCUMENTS

| 3,657,646 | 4/1972 | Zmyslowski et al. | 324/77 A |
| 4,155,352 | 5/1979 | Toglia et al. | 128/733 |
| 4,344,441 | 8/1982 | Radke | 128/733 |
| 4,355,645 | 10/1982 | Mitani et al. | 128/777 |
| 4,585,011 | 4/1986 | Broughton et al. | 128/733 |
| 4,603,703 | 8/1986 | McGill et al. | 128/731 |
| 4,667,513 | 5/1987 | Konno | 73/379 |
| 4,807,642 | 2/1989 | Brown | 128/733 |
| 4,827,934 | 5/1989 | Ekwall | |
| 5,163,440 | 11/1992 | Deluca et al. | 128/733 |

Primary Examiner—Angela D. Sykes
Attorney, Agent, or Firm—Kinney & Lange

[57] ABSTRACT

An amplifier is brought in contact with the muscles of a subject for detecting and amplifying a muscle current, an envelope forming means forms an envelope waveform of the output of the amplifier, and, a time is measured for which the level of the envelope waveform exceeds at least one preset reference level. The shape or position of the display is changed in an image plane depending on the measurement result, or the reference values and the measurement results of the muscle activity are displayed side by side. Strength and/or duration of occlusion by the masticatory muscles of the jaws, and the imbalance in the activity of the pair of left and right muscles can easily be measured and analyzed on the basis of the counting result, but also the analytical result can be used to set the reference values for measuring the envelope waveform level that is optimum for a particular patient.

25 Claims, 7 Drawing Sheets

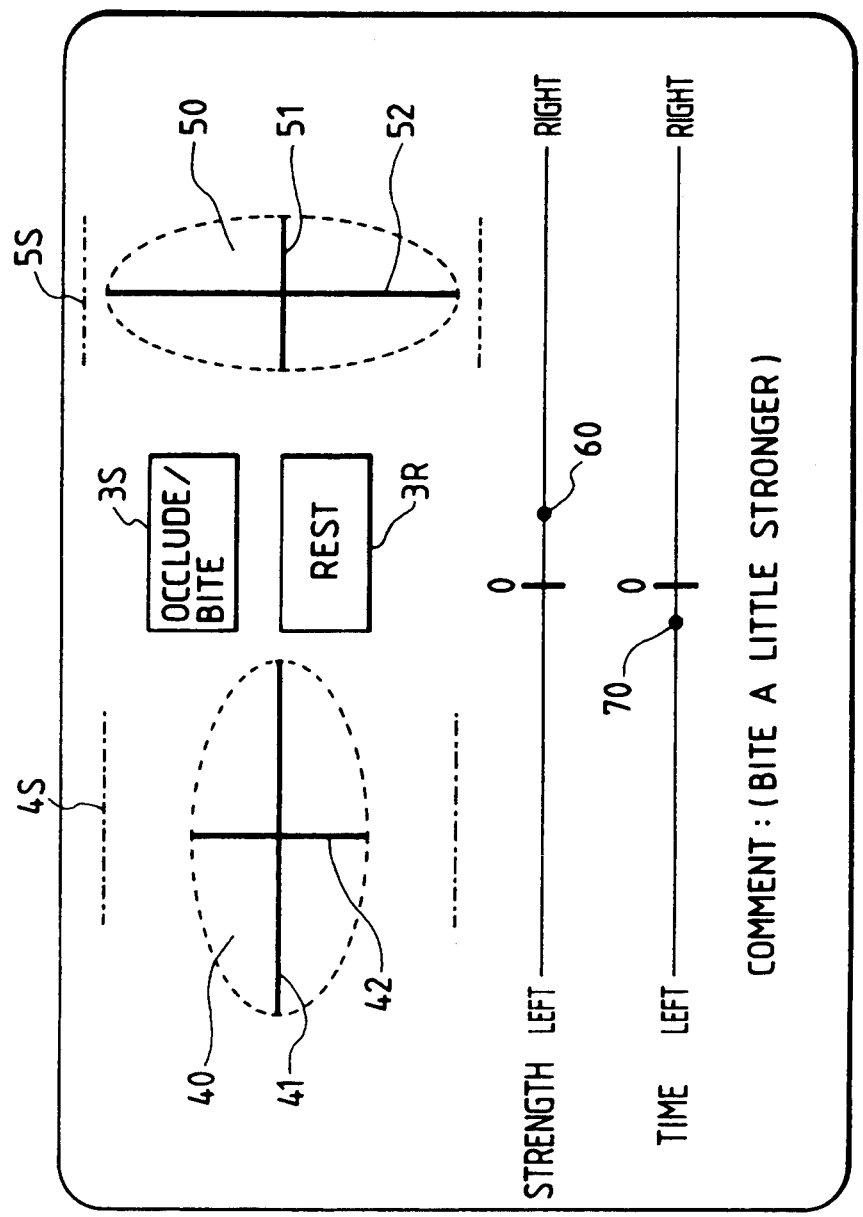

MEASURING SYSTEM FOR VITAL MUSCLE ACTIVITY

This application is a continuation-in-part of U.S. patent application Ser. No. 08/055,921, filed Apr. 29, 1993, which was a continuation of U.S. patent application Ser. No. 07/795,428, filed Nov. 20, 1991, which has been abandoned.

BACKGROUND OF THE INVENTION

1. Field of the Invention

The present invention is related to a measuring system for the muscle activity of a living or vital organism, and particularly to a measuring system for the muscle activity of such as masticatory muscles, which can measure and analyze the change with time in the muscle activity or movement of the masticatory muscles of a human being to determine various set points of the measuring system for the muscle activity, and to a measuring system for the muscle activity of such as masticatory muscles, by which even ordinary people can easily and reliably measure and evaluate the activity or movement of muscles such as masticatory muscles on the basis of the reference value set, on the basis of measurement results of the muscle activity, by a specialist such as a physician or a dentist, without any special training or skill.

2. Description of the Prior Art

Due to the recent rise in the general standard of living, the dietary habits of nations enjoying such a rise have changed and there is a strong tendency that children prefer soft foods and dislike solid ones. For this reason, the development of the masticatory muscles of children has become very poor and various problems due to the insufficient or defective development of the masticatory muscles are indicated.

If the masticatory muscles of children are insufficiently or defectively developed because they like to eat only soft foods, a vicious circle is easily introduced that further causes them to dislike solid foods. An extreme case was reported in which they could finally take only liquid foods.

Apart from such an extreme case, the number of children is increasing who have malocclusion of their maxillary and mandibular teeth, and thus have poorly aligned teeth. In addition, even if such children receive orthodontics, it is often the result that the occlusal condition of the maxillary and mandibular teeth is not maintained and the original irregular teeth alignment is restored again because of the defective development of the masticatory muscles.

Moreover, if one has defectively developed masticatory muscles, the development of the jaw bones is also retarded, and not only are troubles caused in the jaw joint but also such a person cannot strongly occlude his masticatory muscles to close his mouth at times normal to do so and as a result, he will always have open his mouth, or slobber in a worse case.

In addition, since it is thought that biting an object has a deep relationship with the development of the human brain, that the use of masticatory muscles increases the λ-wave of the brain waves by which the ability to concentrate is increased, the appropriate use and training of masticatory muscles are also desirable for the development of intelligence of children.

Conventionally, measuring the activity of vital muscles such as masticatory muscles with an electromyograph has been performed. In this case, usually the output waveform of the electromyograph obtained by setting electrodes on the vital muscles of a subject with the result displayed on an oscilloscope and/or recorded on an appropriate medium. A specialist such as a physician or a dentist observes the measurement result and determines the activity state of the masticatory muscles, and provides appropriate instructions or occlusion to the subject.

The above described prior art had the following problems. That is, to facilitate the development of masticatory muscles, for instance, it is required to continuously hold a strong occlusion state for a certain time in the training and to continue said training for a long period of time. There was a problem in that it was difficult to continue the training and the desired result of the training was not readily obtained, because the training could be provided only under the direction of a specialist. There are also similar problems for the other kinds of muscles.

Accordingly, development is desired of a system for measuring the muscle activity of muscles such as masticatory muscles which can simply be used at home without requiring an attendance of the specialist and which also allows a patient to easily recognize the training effect, and/or of equipment which allows the setting of various measuring devices therefor to properly and easily be performed depending on a patient.

In order to solve the above problems, the present inventors have proposed a system for measuring a vital muscle activity, which can easily measure and analyze the degrees of a vital activity as, for instance, the occlusal strength of the masticatory muscles and the duration thereof as shown in U.S. application Ser. No. 07/795,428.

The problems mentioned above were considerably solved by the above proposal, but it is still desired that such a system make the collection of data on a patient or subject easier, simpler and more accurate. In addition, the system should be more conveniently usable by the patient or subject, allow the muscle activity status to easily be visually recognized, and give appropriate advices or comments as needed.

SUMMARY OF THE INVENTION

It is an object or the present invention to provide a system for measuring a muscle activity which can easily and simply perform the measurement of the muscle activity such as of the masticatory muscles, use the collected results of measurement and analysis to set reference values optimum for a particular patient and/or give appropriate advice or comments to the patient as needed.

It is another object of the present invention to provide a system for measuring a muscle activity, such as of the masticatory muscles, which a patient can easily use during his daily life at home without the attendance of a specialist, and the training effect of which can also easily be recognized by the patient.

The present invention comprises an amplifier means brought in contact with the muscles of a subject for detecting and amplifying a muscle current, an envelope forming means for forming an envelope waveform of the output of the amplifier means, a timer means for measuring a time for which the level of the envelope waveform obtained by the envelope forming means exceeds at least one preset reference level, and a memory means storing the time measured as described above in relation to the corresponding preset reference level.

Also, the present invention is characterized by comprising another timer means for counting each intermittent time for which the level of the envelope waveform exceeds the preset reference level or/and counting the sum of the intermittent times.

The present invention further comprises a display device (for instance, a train or group of light emitting elements) which changes the display mode depending on at least one of the intermittent time durations for which the reference level was exceeded, its maximum value or/and the total sum of the times for which the reference level was exceeded, the distribution of these and the degree of unbalance of the activity of muscles pairing on the left and right sides and the front and rear sides, and/or means for simultaneously or sequentially displaying and recording the activity of the muscles paired as described above and the degree of unbalance thereof on one screen.

Further, the present invention is characterized in that the reference levels are variously preset and each time for which the envelope exceeds each reference level is measured, and on the basis of the measurement result, a specialist can accurately analyze and determine the activity of muscles, such as masticatory muscles, as a basis to set and store various reference levels and training time optimum for cure or training as well as any change thereof. Such stored data can be read out and levels preset as needed if the system is kept and operated by a patient.

Since the envelope waveform of the output of the means for detecting and amplifying the muscle current of a living or vital organism is formed, and the times for which the level of the envelope waveform exceeds a plurality of preset reference levels are counted, stored and displayed for each reference level, not only can the activity of the muscles of the living organism, for instance, the strength and/or the duration of occlusion by the masticatory muscles of the jaws, and the imbalance of the activity of the pair of left and right muscles be easily measured and analyzed on the basis of the counting result, but also the analytical result can be used to set the reference values for measuring the envelope waveform level that are optimum for a particular patient.

Moreover, in the present invention, the envelope waveform of the output of the amplifier means for detecting and amplifying the muscle current is formed, and not only is the time for which the level of the formed envelope waveform exceeds the preset reference level counted and displayed, but also the specialist can optimally set such reference levels on the basis of the result of the previously performed measurement of the activity of muscles such as masticatory muscles; for instance, measurement of the strength of occlusion of the jaws or the duration thereof. Thus, the use thereof requires no particular skill and a subject himself can perform the training of his masticatory muscles while looking at the result of the time counting.

In addition, when the result of the measurement is visually displayed, for instance, if the number of energized light-emitting elements in a train of light-emitting elements, or a shape or a position of the display is changed in an image plane depending on the measurement result, or the reference values and the measurement results of the muscle activity are displayed side by side, discrimination between the results is further facilitated. Also, the ratio of the training time to the time for which the reference level is exceeded by the muscle activity, and the relation between data from muscles which are related, for example, by being paired with each other can be calculated and displayed. Thus, by performing the training while the subject is looking at the results of such various countings and calculations, the training can be performed while maintaining the subject's interest, and a continuous long-term training effort also becomes easy for the subject.

BRIEF DESCRIPTION OF THE DRAWING

FIGS. 5, 6A, 6B, 7A and 7B are graphs showing an exemplary display of the measurement, results of the present invention.

DETAILED DESCRIPTION OF THE PREFERRED EMBODIMENT

Figure 1:
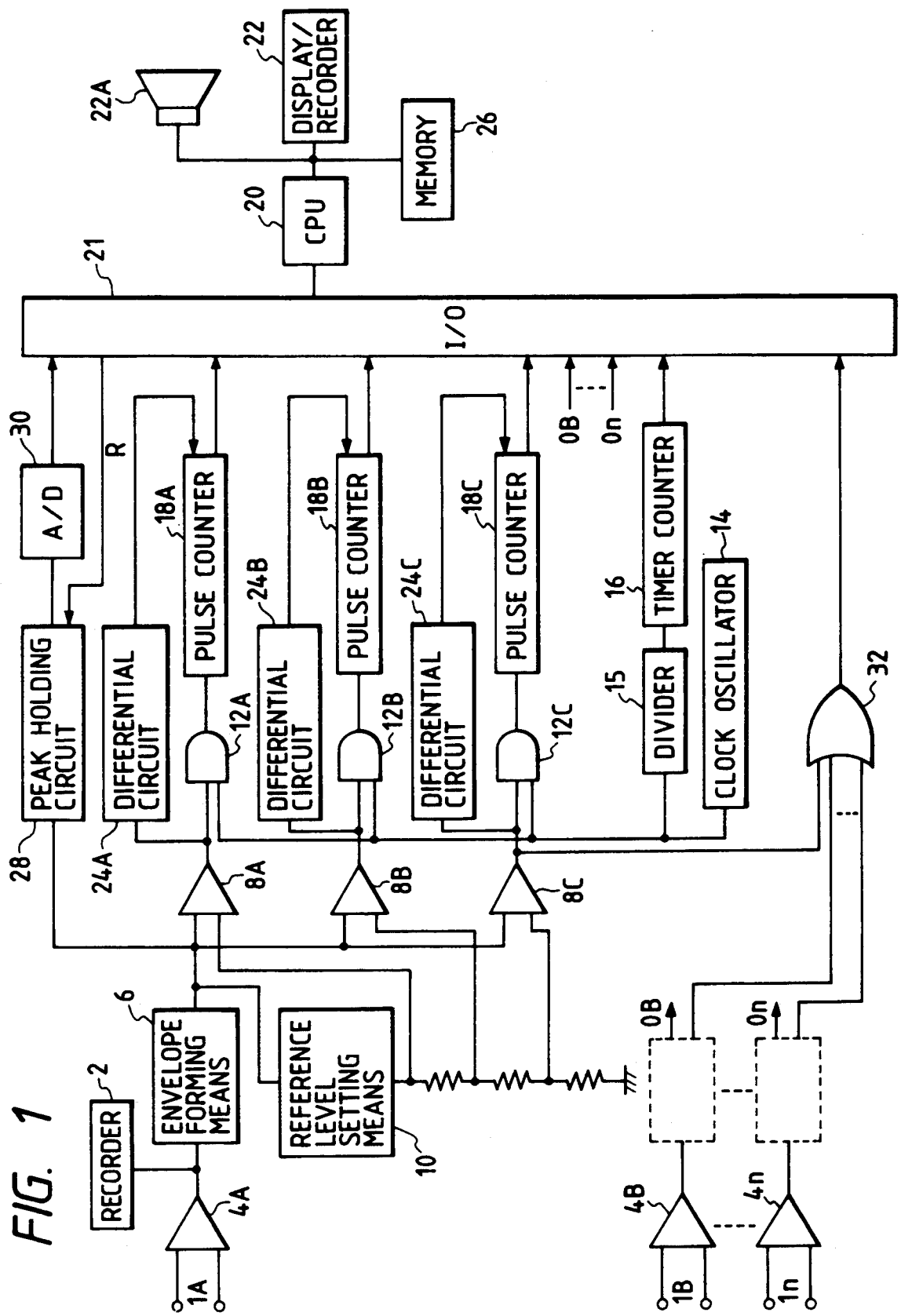
FIG. 1 is a block diagram of an embodiment of the present invention.

Now, the present invention is described in detail with reference to the drawings. FIG. 1 is a block diagram of an embodiment in which the present invention is applied to the measurement of the activity of masticatory muscles.

Each pair of contact electrodes 1A, 1B ... and 1n is appropriately attached to shin adjacent to a muscle to be measured, for example, the masticatory muscle portions beneath the cheeks of a subject, and each of their detection outputs is provided to a corresponding one of amplifiers 4A, 4B ... and 4n. To provide the contact electrodes 1 and 2 and the amplifier 4, a conventional electromyograph apparatus can be used. A muscle current induced in the masticatory muscle is detected by the contact electrodes 1A and amplified by the amplifier 4A when the subject masticates something. The muscle current is an alternating current having frequencies on the order of 300 Hz, and its magnitude or amplitude is substantially proportional to the occlusal force or activity of the muscle.

Figure 2:
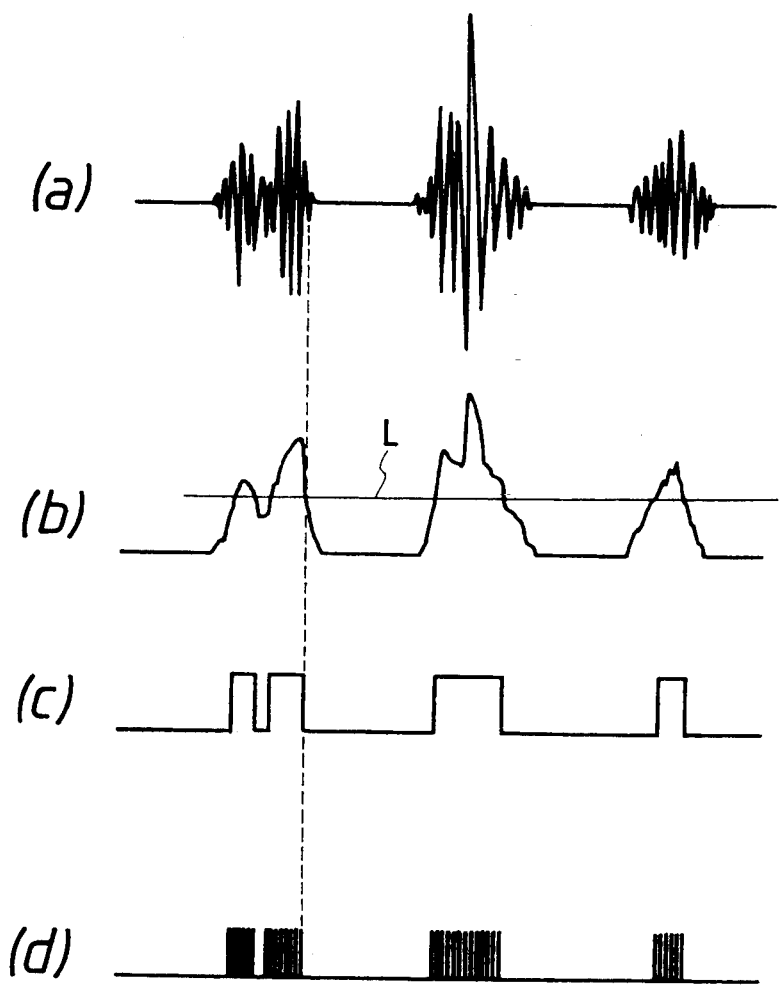
FIGS. 2(a), 2(b), 2(c) and 2(d) are waveform diagrams for explaining the operation of the embodiment of the present invention.

FIG. 2(a) shows an example of the output waveform of the amplifier 4 when the subject intermittently masticates something or occludes his teeth three times. The output of the amplifier 4A is recorded by a recorder 2 and provided to an envelope forming means 6 from which an envelope signal of the waveform (a) is obtained at its output as shown in (b) of FIG. 2. The envelope forming means 6 may be any conventional one, such as that for example, shown in U.S. Pat. No. 4,667,513. The envelope signal is supplied to each of the first inputs of comparators 8A, 8B and 8C. To each of the second inputs of the comparators, a reference level signal from a reference level setting means 10 is provided. The envelope signal may also be supplied to a data recorder which is preferably portable (not shown).

At the second input of the individual comparators, the reference level signals are different in values from each other and automatically set by a reference level setting means 10. The reference level setting means 10 generates an appropriate voltage (not smaller than the peak value) corresponding to the peak output of envelope forming means 6 to determine the reference voltage of each comparator by voltage dividing therefrom. Alternatively, the reference level setting means 10 may be supplied with the output of peak holding circuit 28 instead of envelope forming means 6 as shown. Of course, each reference voltage may be set manually, or only one comparator may be sufficient.

Figure 3:
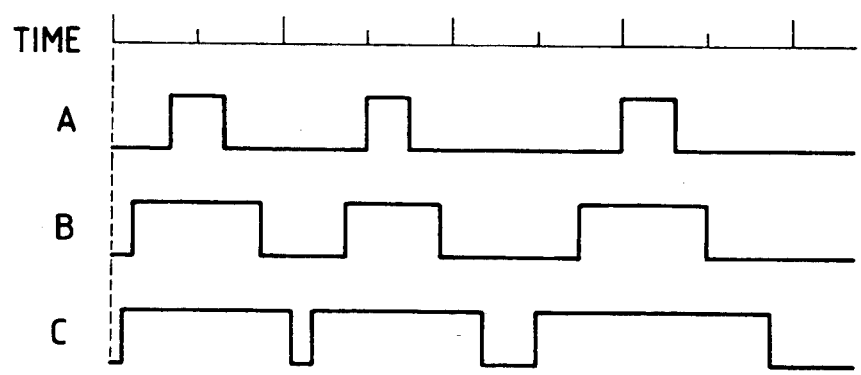
FIG. 3 is a diagram showing an output of each comparator when different reference levels are set for the comparators.

If the reference level for the amplifier 8A is set to be, for instance, L in (b) of FIG. 2, the output of the comparator 8A is a rectangular wave as shown in FIG. 2(c). As is apparent, the rectangular wave of the waveform (c) indicates that the subject bit an object or occluded his teeth during its duration above zero with a force stronger than a certain set level. Remaining comparators 8B and 8C generate similar outputs of rectangular waveforms. However, since the reference voltages of comparators 8A, 8B and 8C become lower in this order, the durations above zero of the output rectangular waves from them become longer in the same order as shown in the corresponding waveforms designated by symbols A, B and C in FIG. 3. From the comparison of the output durations of these plurality of comparators, the general shape and peak value of the input envelope waveform, or the general muscle activity, can be estimated.

The output rectangular waves of the comparators 8A–8C are, respectively, provided to the first inputs of AND circuits 12A–12C, and a clock signal from a clock oscillator 14 is provided to second input of these AND circuits. Thus, at each output of the AND circuits 12A–12C, these are output signals substantially matching the clock signal from clock oscillator 14 only during those times when the rectangular wave is from the corresponding one of comparators 8A–8C has other than a zero value. The pulses in the signals provided at the outputs of AND circuits 12A–12C are counted by a corresponding one of pulse counters 18A–18C connected to these outputs and an accumulating counter (not shown).

Each of differential circuits 24A–24C time differentiates the rectangular waves at the outputs of the corresponding comparators 8A–8C and supplies the falling edge pulses for each pulse to the reset terminal of the corresponding one of pulse counters 18A–18C. Each pulse counter 18A–18C counts the number of the pulses generated at the outputs of AND circuits 12A–12C during the times each rectangular wave is not zero to determine the duration for each such rectangular wave as shown in FIG. 2(d). The count value of each pulse counter 18A–18C is taken into memory 26 under the control of CPU 20 through I/O (interface) 21, and displayed or recorded on display/recorder 22 as needed. Alternatively, the end of the envelope may be determined in CPU 20 instead of the differentiators to reset each pulse counter.

A divider 15 and a timer counter 16 give a time axis for memory, display and recording derived from. The outputs OB, . . . On to signals measured at each of the remaining other series of electrodes contact pairs 1B, . . . 1n are also stored, displayed and recorded in a similar manner as described above. Since the output of the comparator in each series member which has the lowest reference value is supplied as an input to an OR gate 32, the output of the OR gate 32 remains at a high level as long as any comparator is Generating an output. This output is provided to the CPU 20 through the I/O 21 for use as the signal to cause the CPU to start or end the recording.

A display and recording means 22 is preferably a multiplicity of light-emitting elements such as LED's which are unidimensionally arranged, a CRT or a liquid crystal display. The CPU 20 includes a table to associate the count value of the pulse counter with the number of the light-emitting elements to be lit on the display. For example, it operates so that the higher the count value is, the greater number of light-emitting elements are lit. Further, the light-emitting elements may be caused to gradually change their color tone in response to the distance from a reference point similar to the colors of a rainbow, for instance. A display on the CRT or liquid crystal will be described later in detail.

Clearly, the stronger the occlusal force and the longer the duration time thereof, the greater the number of clock pulses passing through the AND circuits 12A–12C, and the number of the light-emitting elements to be lit becomes larger accordingly so that the subject can very easily recognize visually the degree of occlusal force. The volume or pitch of sound may of course be employed instead of the visual display.

An A/D converter 80 converts the peak value of the waveform obtained in a peak holding circuit 28 to a digital value, transfers it through I/O 21 to the CPU 20 where it is stored, displayed or recorded as needed. The peak holding circuit is reset by a signal for determining the end of the envelope in the CPU 20 or by the output of differentiator 24C. 10 The data stored in the memory 26 is transferred to the CPU 20 and analyzed according to a predetermined method. For instance, by comparison of the occlusal condition, time-variation and strength distribution of the waveform, and distribution of the difference among individuals for normal people to the measured data of a patient, the muscle activity of the patient can be determined or diagnosed, and the reference level (of each comparator in FIG. 1) for training and/or cure can be decided.

A timer counter 16 counts the output pulses of a divider 15 used for dividing the output of the clock oscillator 14 to measure the training time and the time from the start of the measurement to the generation of the muscle activity. When a preset time has elapsed, a display thereof is given and the system is stopped as needed.

Sometimes, the balanced activities of left and right muscles paired to each other are desirable in the human body. For instance, for the masticatory muscles, the imbalance of the left and right muscle activities causes many bad effects such as jaw arthropathy, poor mastication due to the unbalanced jaw, weakening of the force of clenching the teeth, reduction in the instantaneous power of clenching, and poor teeth alignment. The activities of the pairs of left and right corresponding muscles should balance in order to keep the posture straight.

If the electrode pairs 1A and 1B in the series of amplifiers 4A and 4B in FIG. 1 are attached to the shin adjacent the left and right masticatory muscles and the obtained outputs are detected and displayed at the same time, the degree of balance of the left and right masticatory muscles can be easily and accurately diagnosed. FIG. 5 shows an example of such a display, which is displayed on display/recorder 22 by means of a liquid crystal or CRT under the control of the CPU 20 in FIG. 1.

In the same figure, ellipse 40 represents the activity of the left masticatory muscle, the length of horizontal line 41 is the duration of the muscle activity (the duration of the output rectangular wave of a comparator), and the length of vertical line 42 corresponds to the peak value of the muscle current or envelope in the duration. Ellipse 50 represents the activity of the right masticatory muscle, and horizontal and vertical lines 51 and 52 similarly represent the duration and peak value, respectively. Alternatively, the ellipse and at least one of the two line segments can be omitted to display either the peak value or the duration, or the quiescent time can be displayed instead. As shown by chain lines 4S and 5S in FIG. 5, it is effective in practical use to display straight lines representing the maximum peak value of the muscle current or envelope when the subject occludes as strongly as possible, or to display concentric circles as scale lines, though not shown in the figure. In this case, the maximum peak value for the strongest occlusion may be displayed by one of the scale line circles, preferably with a color different from others. By this means, the percentage of the maximum occlusal force reached at each occlusion during the measurement (for instance, when food is taken in, chewed and swallowed), or whether the muscle contraction is optimally controlled in response to the properties of the food, can be recorded, viewed and confirmed in real time.

The display position of point 60 represents the balance of the activity strength of the pair of left and right muscles (the difference between or ratio of them). The zero position is a completely balanced state, the display position of the point leaning to the right represents that the right muscle activity is stronger than the left one, and the displacement distance from the zero position represents the degree of imbalance. Point 70 shows a matter similar to point 60 concerning the duration of the muscle activity. Only one of these points 60 and 70 can be displayed or the quiescent time can be added. In addition, they may be displayed by the length of a line segment from the reference point 0 instead of the position of a point.

Figure 6A:
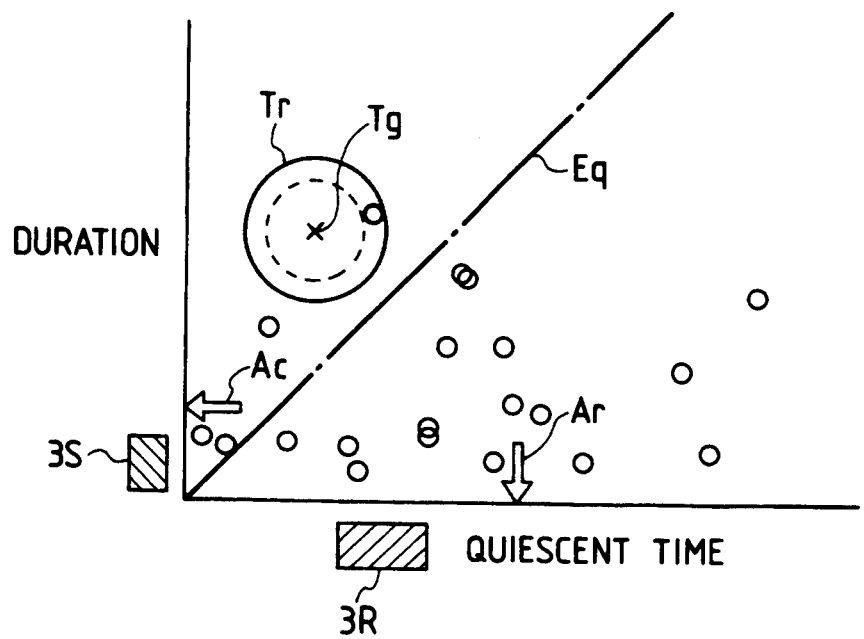
Figure 6B:
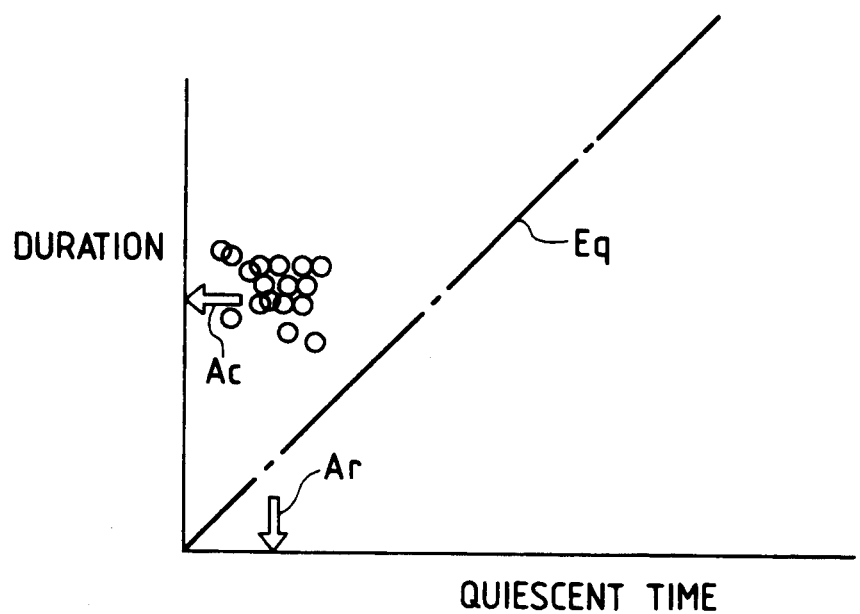
Figure 7A:
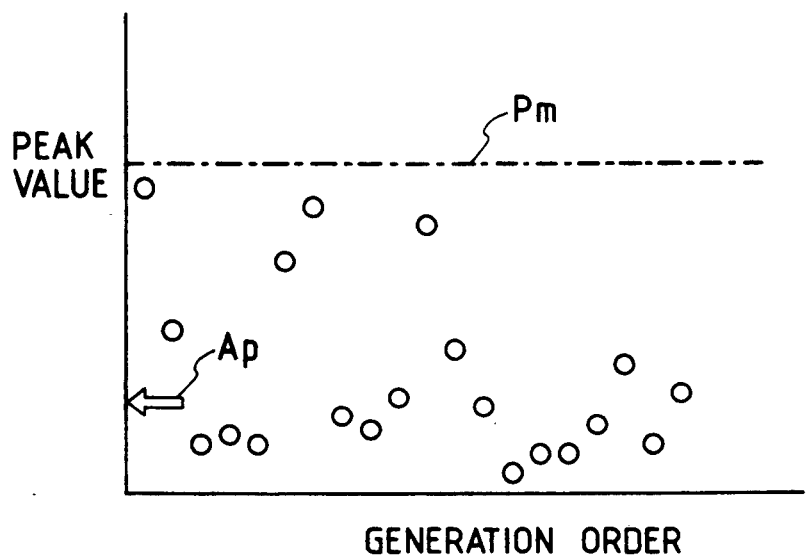
Figure 7B:
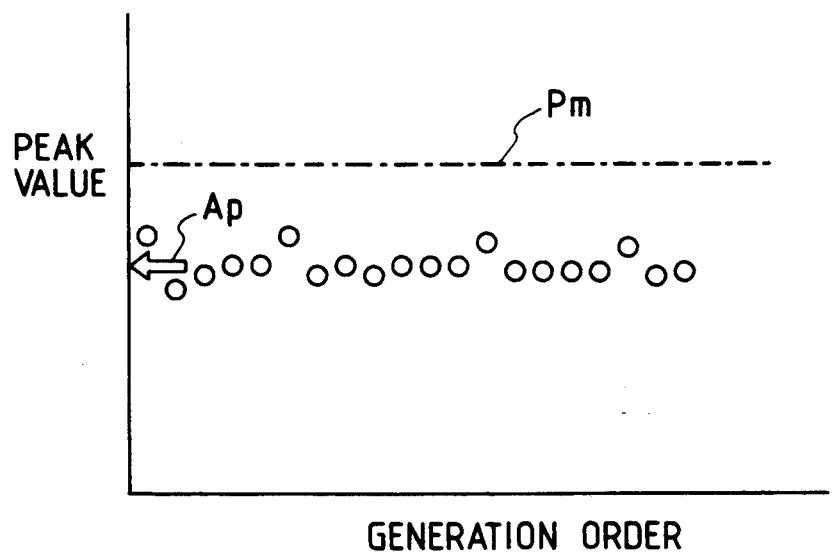

Another example of the display screen showing the result of the muscle activity measurement is shown in FIGS. 6A, 6B, 7A and 7B. In FIGS. 6A and 6B, the ordinate is the duration of one muscle activity (for instance, occlusion) and the abscissa is the quiescent time or generation interval of muscle activity of such as occlusion. The ordinate of FIGS. 7A and 7B is the peak value of the envelope and the abscissa is the occurrence order in time series, and horizontal line Pm represents the peak value when the subject occludes most strongly or as strongly as possible. The mean values of these respective measured values may be moving averages calculated for the appropriate number of times occlusion occurs sequentially, and displayed on the same screen as shown by arrows Ac, Ar and Ap, or displayed graphically or numerically (not shown in the figures).

FIGS. 6A and 7A show an example of the initial measured data when a normal subject takes food into his mouth (after biting it off), and of the measured data of a subject having malocclusion. The values of the duration and quiescent time (generation interval) for each occlusion and the envelope peak value are seen to be widely scattered. FIGS. 6B and 7B show an example of the measured data when a normal subject has almost finished the biting of the food, and of measured data of the subject whose occlusal condition has been improved. The duration and quiescent time for each occlusion can be seen to concentrate on substantially one point and the envelope peak value or the muscle current output is stabilized as well.

It is useful to additionally display a straight line Eq corresponding to the relation of Duration-Quiescent time as shown in FIGS. 6A and 6B, or to display a target point Tg the coordinate of which is defined by the combination of the reference values of the duration and quiescent times and/or a circle Tr around the point Tg representative of the area for permissible deviation from point Tg. The subject can visually recognize by himself how much the activity of his muscle deviates from the targets through these displays, and thus they are expected to promote the effect of training.

In addition the to displays of FIGS. 6A and 6B and FIGS. 7A and 7B, by sequentially or simultaneously displaying the intermediate data on the screen for a predetermined number of occlusions the masticatory state changes or improvements can be recorded, viewed and confirmed in real time. Since the subject can measure and monitor the activity of the masticatory muscles by himself, and realize the relationship between the feeling when he clenches his teeth and the balanced state of the left and right muscle activities while looking at least one display of FIGS. 5, 6A, 6B, 7A and 7B, a good training effect can be achieved.

Moreover, to correct the masticatory action, it is possible that the reference or target values of the individual measured values be decided on the basis of the result of the previously performed measurement of the strength, duration, quiescent time and balance status of occlusion which are prestored in the memory 26, and the deviation of each measured value therefrom is calculated. Based on the deviation, appropriate comments in the form of notes on the cure and training or instructions on the masticatory action (for instance, change of the strength, rhythm or interval of biting) are given to the subject by an appropriate display such as written characters, voice, or selection or blinking of a display. An example of a character display is shown in the lower part of FIG. 5. It is also possible to show to the subject instructions of duration and/or quiescent time by visual display 3S, 3R as shown in the upper center of FIG. 5 and along the coordinate axes of FIG. 6A, or give the subject such instructions aurally through the speaker 22A and/or tactually by appropriate unshown means. The instructions of display 3S, 3R may be given in blink or change of colour of the display. It is expected to improve the training effect by giving the subject instructions of muscle activity and quiescent period in at least one of forms mentioned above, according to the subject's ability to understand.

Although the present invention has been described by taking an example in which it is used for measuring the activity of masticatory muscles, it will easily be understandable that the present invention may also be applied to measurement or correction of other ordinary vital muscles.

Figure 4:
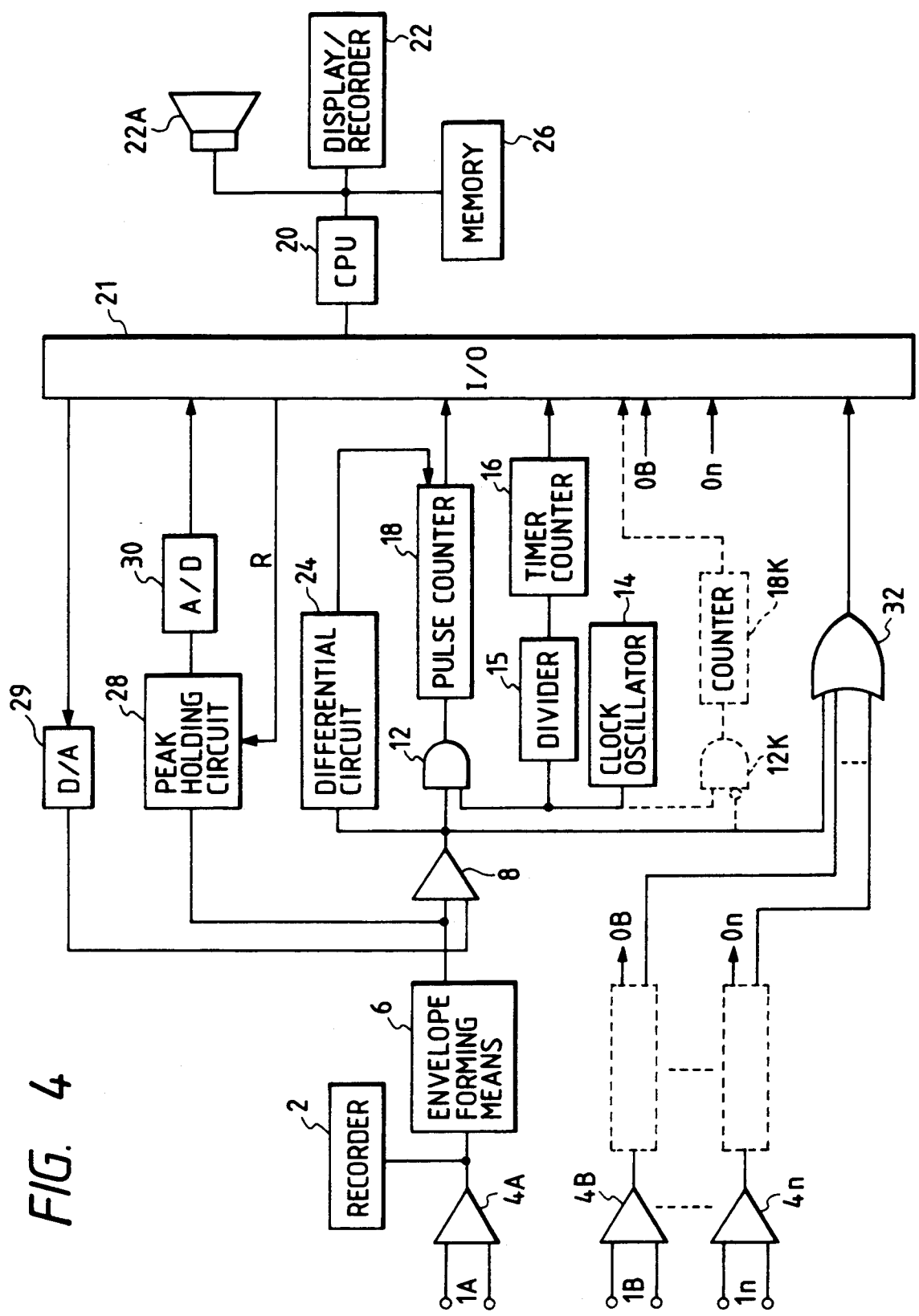
FIG. 4 is a block diagram showing an example of another embodiment of the present invention.

FIG. 4 is a block diagram showing another embodiment of the present invention, and particularly it is a system for measuring a muscle activity which is suitable for a patient to carry with him in daily life for continuously performing measurement, training and cure. In the same figure, the same symbols as used in FIG. 1 represent the same or identical portions. As seen from the comparison with FIG. 1, the system of FIG. 4 corresponds to the system of FIG. 1 except that the reference level settings, comparators, AND circuits and counters are limited to one set. The various changes and corrections which were previously described with reference to FIG. 1 can also be applied to the system of FIG. 4 as a matter of course.

The system of FIG. 4 is characterized in that, based on the various data on a particular patient which were previously gathered by the system of FIG. 1, a specialist such as a physician prestores in memory 26 the reference level of comparator 8, the training hours per day, and notes or instructions on the cure and training, or the change value or the correction calculation formula of the reference level and/or the training hours per day involved in the increase of the training effect. These are supplied to comparator 8, display/recorder 22 and the like at the determination of CPU 20 based on the measured values up to the present or the tendency of change thereof.

When a patient carrying the present system turns on the power, CPU 20 sets in comparator 8 the reference level prestored in memory 26, or the reference level calculated on the basis of the peak value of the envelope obtained by a preliminary occlusion test of the patient. By this means, various data on the muscle activity similar to those described with reference to FIG. 1 are read into memory 26, and the measurement result is displayed on display/recorder 22 as shown in at least one of FIGS. 5–7B.

An accumulator counter for clock pulses from the AND circuit and mean value circuit may be included in the device of FIG. 1 or FIG. 4, which is described later in reference to FIG. 8, although they are not shown in FIGS. 1 or 4.

in addition, means for setting the target values of each counter, mean value circuit and accumulator counter may be provided, and when the respective output values reach the target values, a display to that effect may be provided or the system may be stopped. FIG. 8 shows a block diagram to be added to FIGS. 1 or 4 for the purpose mentioned just above.

Figure 8:
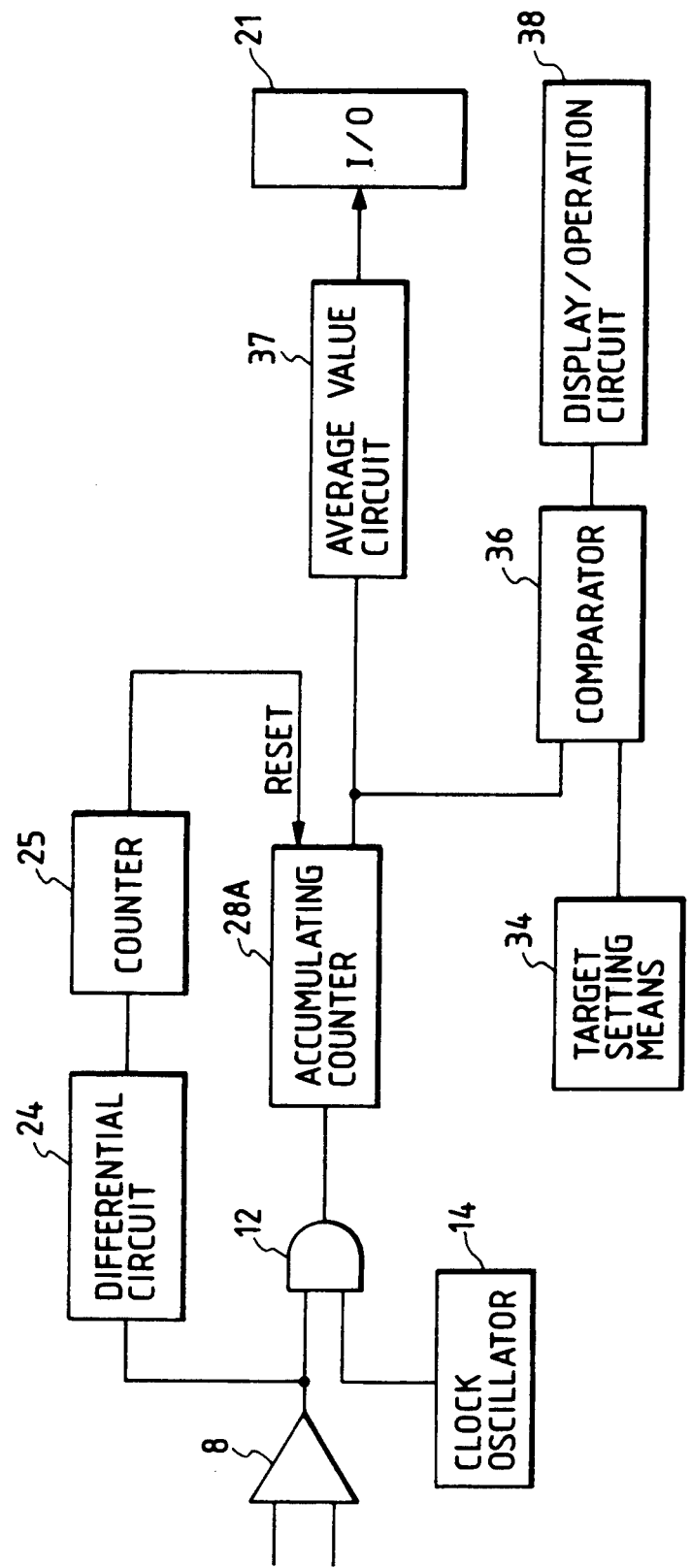
FIG. 8 is a block diagram showing the main portions of still another embodiment of the present invention.

In FIG. 8, the accumulating counter 28A accumulates the total number of clock pulses passing through the AND circuit 12 for a predetermined time or a predetermined number of envelope waves by which the sum of the times for which the subject bit the object or occluded his teeth can be measured. The average value circuit 37 is to average the count value of the accumulating counter 28A. The average value can also be displayed by providing means similar to the display and recording means 22 and/or saved in the memory 26.

In a target setting means 34, a target value of the total sum times mentioned above is preset, and compared in a comparator 36 with the output of the accumulating counter 28A. The comparator 36 provides an output when the sum of the times for which the subject has bit the object or occluded his teeth with a force greater than the given set level reaches the target value. This allows a display and operation circuit 38 to display that the target value was reached and/or stop the system. Further, measuring the generation interval (repetition cycle) of pulses, namely, the time from the fall of the preceding pulse to the rise of the next pulse, is also useful for diagnosing and measuring the cycle or rhythm of the masticatory movement. The arrangement for measuring the generation interval of pulses or the quiescent time of the muscle activity can easily be implemented by, as shown by dotted lines in FIG. 4, adding AND circuit, having the inverted signal of the output of comparator 8 and the output of clock oscillator 14 (or divider 15) as the two inputs thereof, and counter 18K for counting the output clock of AND circuit 12K. It is obvious that a similar arrangement can also be provided for FIG. 1. An accumulating counter for clock signals output from AND circuit, target setting means and average circuit for count value of pulse counter may be additionally provided in FIGS. 1 and 4, although they are not shown.

As apparent from the above description, in accordance with the present invention, by gathering various rectangular wave signals through discrimination of the output waveform with a plurality of reference levels and analyzing them, the muscle activity of a live or vital organism, for instance, the occlusion strength of the jaws and the duration of the occlusion can easily be measured and analyzed, and the use of the results of the measurement and analysis allows the setting of the reference value for the treatment and training optimum for a particular patient.

Also, in accordance with the present invention, the time for which the patient has bitten with a force stronger than the given set value, strength of occlusion, balance of occlusion, and the like can visually be recognized not only from the display of the counter but also from the lighting state of such as linearly arranged LED's or graphs shown in FIGS. 5, 6A, 6B, 7A and 7B. Thus, the patient himself discriminates his own occlusion force, continues the training, and makes an evaluation without any particular direction by a specialist.

In consequence, it is easy for the patient or subject to adjust the occlusal force while looking at the display of the examination result and try to bite with a force greater than the set value, whereby he can accomplish the increasing of his muscular strength by training.

As the subject can measure and display the duration and strength of each muscle activity or the balance of the left and right pairing muscles, he can see the measurement result before he forgets the feeling of the muscle activity, and can also receive appropriate instructions or comments during the training so that the correction is easy and effective. In addition, the set value can properly be set according to the condition of the subject so that optimum setting is easily accomplished. Also, it is possible to measure the percentage of the time the subject has bitten with the occlusal force larger than the set value during his training, to count the total time of the training, and/or to calculate and display the ratio of the training time or the time for which he has bitten with the occlusal force larger than the set value to the total time, which are useful.

Since the system of the present invention is simple and can be made in small size for portable use, a subject can always carry the device with him for training in all times and every places, whereby better training results can be expected.

What is claimed is:

1. A system for measuring muscle activity of a living organism comprising:
    a muscle current detection means suitable for being brought into electrical contact with a subject living organism adjacent a selected muscle thereof for detecting muscle current to provide a corresponding output signal waveform having therein at least one oscillatory episode with oscillation peaks therein of various amplitudes;
    an envelope waveform forming means for forming envelope waveforms representing muscle activity with each being formed for a corresponding one of those oscillatory episodes occurring in the output waveform of the muscle current detection means and based on said peak amplitudes therein;

a timer means for measuring the duration of time for which the values of each envelope waveform formed by the envelope waveforming means are beyond a selected reference level to indicate those durations that said muscle activity was beyond a corresponding muscle activity level;

a memory means for storing the time durations measured by the timer means and user instructions; and a display means for providing an indication of durations of the measured for said envelope waveforms and selected user instructions based on such durations of time measured.

2. The system of claim 1 wherein said memory means is also for storing user target performance values for the measured time durations, and wherein said display means displays a selected user target performance value.

3. A system for measuring muscle activity of a living organism comprising:

a muscle current detection means suitable for being brought into electrical contact with a subject living organism adjacent a selected muscle thereof for detecting muscle current to provide a corresponding output signal waveform having therein a plurality of oscillatory episodes each with oscillation peaks therein of various amplitudes;

an envelope waveform forming means for forming envelope waveforms representing muscle activity with each being formed for a corresponding one of those oscillatory episodes occurring in the output waveform of the muscle current detection means and based on said peak amplitudes therein;

a timer means for measuring the duration of first reference level active time for which the values of each envelope waveform formed by the envelope forming means are beyond a selected first reference level to indicate those durations that said muscle activity was beyond a corresponding muscle activity level, and for measuring the duration of quiescent time between successive first reference level active the durations to indicate those durations that said muscle activity was relatively quiescent;

a memory means for storing the time durations measured by the timer means; and a display means for providing an indication of durations of time measured for said envelope waveforms.

4. The system of claim 3 wherein there are a plurality of selected reference levels of values differing from one another including a lowest magnitude reference level serving as said first reference level, and said timer means measures the duration of active time for which the values of each envelope waveform formed by the envelope waveforming means are beyond a corresponding one of said selected reference levels to indicate those durations that said muscle activity was beyond a corresponding muscle activity level.

5. The system of claim 3 wherein said timer means comprises a comparator for comparing the values of each envelope waveform to a selected reference level to provide an output signal at an output thereof indicating relative magnitudes thereof, a clock signal source providing a clock signal having clock periodic pulses therein, an AND logic gate circuit to which the output of the comparator and the output of the clock signal source are coupled to provide gate output signal periodic pulses at an output thereof during the durations determined by the comparator output signal, and a counter means coupled to the AND logic gate circuit output for counting the gate output signal periodic pulses.

6. The system of claim 5 wherein user target performance values are also stored in said memory means for at least one of the measures of first reference level active time duration and quiescent time duration, and wherein said timer means comprises a further comparator for comparing the count value of said counter means to said user target performance values to provide an output signal at an output thereof indicating relative magnitudes thereof, and wherein said display means receives said further comparator output signal to provide an indication of differences between said count values and said user target performance values.

7. The system of claim 6 wherein said display means provides an indication of measurement values for the measures of successive quiescent and first reference level active time durations for a plurality of envelope waveforms as intersection indicators on a first graph having active time duration and quiescent time duration as axes thereof.

8. The system of claim 7 wherein said display means displays a plurality of graphs similar to and including said first graph each providing an indication of measurement values for the measures of successive quiescent and first reference level active time durations for a corresponding plurality of envelope waveforms.

9. The system of claim 7 wherein said display means displays in said first graph a line representing equal values of first reference level active time durations and quiescent time durations.

10. The system of claim 7 wherein user target performance values are also stored in said memory means or the measures of first reference level active time duration and quiescent time duration, and wherein said display means displays in said first graph a selected user target performance value as another intersection indicator serving the center of a circle displayed thereabout of selected radius.

11. The system of claim 7 wherein user target performance values are also stored in said memory means for the measures of first reference level active time duration and quiescent time duration, and wherein said display means displays in said first graph a selected user target performance value as another intersection indicator and an indication of permissible deviations therefrom of measurement values for the measures of successive quiescent and first reference level active time durations of envelope waveforms.

12. The system of claim 7 wherein said indication of permissible deviations from said selected user target performance value is a circular area thereabout.

13. The system of claim 7 wherein said display means also provides an indication of the mean value of said measurement values for at least one of the measures of quiescent and first reference level active time durations.

14. The system of claim 3 further comprising a peak value detection means for measuring maximum values for each said envelope waveform as peak values, and wherein said display means provides an indication of measurement values of the peak value measure for a plurality of envelope waveforms as intersection indicators on a first graph having peak value and envelope waveform occurrence order as axes thereof.

15. The system of claim 14 wherein said display means provides a further indication of a greatest peak value from among said peak values corresponding to the maximum value of muscle activity.

16. The system of claim 14 wherein said display means displays a plurality of graphs similar to and including said first graph each providing an indication of measurement values for the peak value measure for a corresponding plurality of envelope waveforms versus the occurrence order thereof.

17. The system of claim 14 wherein said display means also provides an indication of the mean value of said measurement values for the peak value measure.

18. The system of claim 3 further comprising a peak value detection means for measuring maximum values for each said envelope waveform as peak values, and wherein user target performance values are also stored in said memory means for at least one of the measures of active time duration, quiescent time duration and peak value, and wherein user instructions are also stored in said memory means such that said display means provides indications of one or more said instructions to a user selected from those stored in said memory means on the basis of the magnitude of deviations of a measured value from a corresponding user target performance value, said display means providing at least one of visual, aural and tactual kinds of said indications of said instructions.

19. The system of claim 3 wherein user instructions are also stored in said memory means such that said display means provides indications of one or more said instructions to a user selected from those stored in said memory means as to the performance of muscle activity in connection with obtaining measurement values for the measures of first reference level active and quiescent time durations.

20. A system for measuring muscle activity of a living organism comprising:
a muscle current detection means suitable for being brought into electrical contact with a subject living organism adjacent each of a selected pair of muscles thereof for detecting muscle current in each member thereof to provide corresponding output signal waveforms for each member with each output signal waveform having therein at least one oscillatory episode with oscillation peaks therein of various amplitudes;
an envelope waveforming means for forming envelope waveforms representing muscle activity of each of said pair of muscles with each envelope waveform formed for a member of said pairs of muscles corresponding to one of those oscillatory episodes occurring in the output waveform of the muscle current detection means for that member and based on the peak amplitudes therein;
a timer means for measuring the duration of active time for which the values of each envelope waveform formed by the envelope waveforming means for a member of said muscle pair is beyond a corresponding selected reference level to indicate those durations that said muscle activity for each said member was beyond a corresponding muscle activity level;
a memory means for storing the time durations measured by the timer means; and
a display means tier providing an indication of durations of time measured for said envelope waveforms.

21. The system of claim 20 further comprising a calculating means for calculating a degree of balance between the muscle activity of said pair of muscles based on the envelope waveforms corresponding to each, and wherein said display means provides an indication of the degree of balance between the muscle activities of said pair of muscles.

22. The system of claim 21 wherein said indication of the degree of balance is the distance of an indicator from a reference point representing a selected one of the value of the difference between the muscle activities of said pair of muscles and the value of the ratio of the muscle activities of said pair of muscles.

23. The system of claim 20 wherein each said output signal waveform provided by said muscle current detection means corresponding to one of said pair of muscles has a plurality of oscillatory episodes therein, and wherein said timer means is further for measuring the duration of quiescent time between successive active time durations for each member of said pair of muscles to indicate those durations that said muscle activity for that member was relatively quiescent, and further comprising a peak value detection means for measuring maximum values for each said envelope waveform for each member of said pair of muscles, said display means providing an indication of a measurement value for a member of said pair of muscles for at least one of the measures of active time duration, quiescent time duration or peak value, or an average of a plurality of values for one of these measures.

24. The system of claim 23 wherein said display means provides indications of measurement values for a member of said pair of muscles for at least two of the measures of active time duration, quiescent time duration or peak value, with the two indications being the lengths of two orthogonal lines intersecting one another at the centers of each together serving as a major and minor axes of an ellipse.

25. The system of claim 24 wherein said display means provides a further indication of—a greatest peak value for a member of said pair of muscles corresponding to the maximum value of muscle activity of that muscle.

* * * * *

UNITED STATES PATENT AND TRADEMARK OFFICE
CERTIFICATE OF CORRECTION

PATENT NO. : 5,368,043

DATED : November 29, 1994

INVENTOR(S) : YUJIRO SUNOUCHI, HIROSHI SAKAMOTO

It is certified that error appears in the above-indentified patent and that said Letters Patent is hereby corrected as shown below:

On the Title page of the Patent, at line 5 of [57] ABSTRACT, delete "for", insert --by a timer during--

Col. 2, line 24, delete "an attendance of the specialist", insert --the attendance of a specialist--

Col. 2, lines 42-43, delete "advices", insert --advice--

Col. 4, line 24, delete "measurement,", insert --measurement--

Col. 4, line 37, delete "shin", insert --skin--

Col. 4, line 67, delete "values", insert --value--

Col. 5, line 34, delete "these", insert --there--

Col. 5, line 68, delete "Generating", insert --generating--

Col. 6, line 25, delete "converter 80", insert --converter 30--

Col. 6, line 26, before "waveform", insert --envelope--

Col. 6, line 31, delete "24C.10", insert --24C.--

Col. 6, line 60, delete "shin", insert --skin--

Col. 8, line 15, delete "In addition the to", insert --In addition to the--

UNITED STATES PATENT AND TRADEMARK OFFICE
CERTIFICATE OF CORRECTION

PATENT NO. : 5,368,043
DATED : November 29, 1994
INVENTOR(S) : YUJIRO SUNOUCHI, HIROSHI SAKAMOTO It is certified that error appears in the above-indentified patent and that said Letters Patent is hereby corrected as shown below:

Col. 14, line 11, delete "tier", insert --for--

Signed and Sealed this

Twenty-first Day of March, 1995

Attest:

BRUCE LEHMAN

Attesting Officer    Commissioner of Patents and Trademarks